US00PP15353P2

(12) United States Plant Patent
Smith

(10) Patent No.: US PP15,353 P2
(45) Date of Patent: Nov. 23, 2004

(54) ***CHRYSANTHEMUM* PLANT NAMED 'YOCARMELLA'**

(50) Latin Name: *Chrysanthemum×morifolium*
Varietal Denomination: Yocarmella

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/764,890

(22) Filed: Jan. 26, 2004

(51) Int. Cl.[7] ..... A01H 5/00

(52) U.S. Cl. ..... Plt./286

(58) Field of Search ..... Plt./286

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of *Chrysanthemum* plant named 'Yocarmella', characterized by its upright and somewhat outwardly spreading plant habit; freely branching habit; dense and full plant habit; uniform and freely flowering habit; small decorative-type inflorescences with elongated oblong-shaped ray florets; red-colored ray florets; and natural season flowering in mid October in the Northern Hemisphere.

2 Drawing Sheets

Botanical classification/cultivar designation: *Chrysanthemum×morifolium* cultivar Yocarmella.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Yocarmella'.

The new cultivar is a product of a planned breeding program conducted by the Inventor in Salinas, Calif., and Alva, Fla. The objective of the breeding program is to create new garden-type *Chrysanthemum* cultivars having inflorescences with desirable inflorescence forms, attractive floret colors and good garden performance.

The new *Chrysanthemum* originated from a cross-pollination made in January, 2001 in Salinas, Calif. of a proprietary *Chrysanthemum×morifolium* seedling selection identified as code number 98-M305, not patented, as the female, or seed, parent with a proprietary *Chrysanthemum× morifolium* seedling selection identified as code number 93-L372002, not patented, as the male, or pollen, parent. The new *Chrysanthemum* was discovered and selected by the Inventor as a single flowering plant within the progeny of the stated cross-pollination grown in a controlled environment in Alva, Fla. in October, 2001. The selection of this plant was based on its desirable inflorescence form, attractive ray floret color and good garden performance.

Asexual reproduction of the new cultivar by terminal vegetative cuttings taken in a controlled environment in Alva, Fla. since December, 2001, has shown that the unique features of this new *Chrysanthemum* are stable and reproduced true to type in successive generations.

SUMMARY OF THE INVENTION

The cultivar Yocarmella has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yocarmella'. These characteristics in combination distinguish 'Yocarmella' as a new and distinct cultivar:

1. Upright and somewhat outwardly spreading plant habit.
2. Freely branching habit; dense and full plants.
3. Uniform and freely flowering habit.
4. Small decorative-type inflorescences with elongated oblong-shaped ray florets.
5. Red-colored ray florets.
6. Natural season flowering in mid October in the Northern Hemisphere.

In side-by-side comparisons conducted in Alva, Fla., plants of the new *Chrysanthemum* differed from plants of the female parent, the proprietary seedling selection identified as code number 98-M305, in the following characteristics:

1. Plants of the new *Chrysanthemum* flowered about two weeks later than plants of the female parent selection when grown under natural season conditions.
2. Plants of the new *Chrysanthemum* flowered about five to seven days later than plants of the female parent selection when grown under artificial short day/long night photoperiodic conditions.
3. Plants of the new *Chrysanthemum* and the female parent selection differed in ray floret coloration as plants of the female parent selection had dark lavender-colored ray florets.

In side-by-side comparisons conducted in Alva, Fla., plants of the new *Chrysanthemum* differed from plants of the male parent, the proprietary seedling selection identified as code number 93-L372002, in the following characteristics:

1. Plants of the new *Chrysanthemum* flowered a few days later than plants of the male parent selection under natural season conditions.
2. Inflorescences of plants of the new *Chrysanthemum* had fewer disc florets than inflorescences of plants of the male parent selection.

Plants of the new *Chrysanthemum* can be compared to plants of the *Chrysanthemum* cultivar Raquel, disclosed in U.S. Plant Pat. No. 8,982. In side-by-side comparisons conducted in Alva, Fla., plants of the new *Chrysanthemum* differed from plants of the cultivar Raquel in the following characteristics:

1. Plants of the new *Chrysanthemum* were smaller, more uniform and more rounded than plants of the cultivar Raquel.
2. Plants of the new *Chrysanthemum* flowered more uniformly than plants of the cultivar Raquel.

Plants of the new *Chrysanthemum* can also be compared to plants of the *Chrysanthemum* cultivar Mistretta, not patented. In side-by-side comparisons conducted in Alva, Fla., plants of the new *Chrysanthemum* differed from plants of the cultivar Mistretta in the following characteristics:

1. Plants of the new *Chrysanthemum* were smaller and more rounded than plants of the cultivar Mistretta.
2. Plants of the new *Chrysanthemum* flowered more uniformly than plants of the cultivar Mistretta.
3. Plants of the new *Chrysanthemum* had smaller inflorescences than plants of the cultivar Mistretta.
4. Plants of the new *Chrysanthemum* flowered a few days earlier than plants of the cultivar Mistretta under natural season conditions.
5. Ray florets of plants of the new *Chrysanthemum* faded slower than ray florets of plants of the cultivar Mistretta.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yocarmella' grown in a container.

The photograph on the second sheet comprises a close-up view of typical inflorescences of the cultivar 'Yocarmella'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Alva, Fla. during the winter in a fiberglass-covered greenhouse under conditions and practices which approximate those generally used in commercial garden-type *Chrysanthemum* production. One cutting was planted in a 15.25-cm container in early December, 2002. Plants were pinched one time, that is, the terminal apex was removed to enhance branching, at the end of December. One week after the pinch, plants were exposed to short day/long night photoperiodic treatments until flowering. During the production of the plants, day temperatures averaged 26° C. and night averaged 18° C. Measurements and numerical values represent averages for typical flowering plants.

Botanical classification: *Chrysanthemum×morifolium* cultivar Yocarmella.

Commercial classification: Decorative-type garden *Chrysanthemum*.

Parentage:

*Female, or seed, parent.*—Proprietary *Chrysanthemum×morifolium* seedling selection identified as code number 98-M305, not patented.

*Male, or pollen, parent.*—Proprietary *Chrysanthemum×morifolium* seedling selection identified as code number 93-L372002, not patented.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with mounded crown. Stems initially upright, then somewhat outwardly spreading. Freely branching with lateral branches potentially developing at every node. Moderately vigorous.

*Plant height.*—About 19 cm.

*Plant diameter.*—about 21 cm.

*Lateral branches.*—Length: About 18 cm. Diameter: About 3.5 mm. Internode length: About 1.5 cm. Aspect: Upright and somewhat outwardly spreading. Texture: Pubescent. Color: 146A.

*Foliage description.*—Leaf arrangement: Alternate. Length: About 5 cm. Width: About 3.6 cm. Apex: Mucronate. Base: Truncate. Margin: Palmately lobed, sinuses divergent. Texture, upper surface: Slightly pubescent. Texture, lower surface: Pubescent; veins prominent. Color: Developing and fully expanded foliage, upper surface: 147A. Developing and fully expanded foliage, lower surface: 147B. Venation, upper surface: 147A. Venation, lower surface: 147B. Petiole length: About 1.5 cm. Petiole diameter: About 2 mm. Petiole color, upper surface: 147A to 147B. Petiole color, lower surface: 147B.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. About eleven inflorescences per lateral branch.

*Flowering response.*—Under natural season conditions, plants flower in mid October in the Northern Hemisphere.

*Inflorescence bud (before showing color).*—Height: About 5 mm. Diameter: About 7 mm. Shape: Oblate. Color (lower surface of phyllaries): Close to 147A.

*Inflorescence size.*—Diameter: About 3.5 cm. Depth (height): About 1.5 cm. Disc diameter: About 2.5 mm. Receptacle diameter: About 3 mm.

*Ray florets.*—Shape: Elongated oblong. Length: About 1.75 cm. Corolla tube length: About 3 mm. Width: About 5 mm. Apex: Acute to emarginate. Margin: Fused. Texture: Smooth, glabrous; velvety. Surface: Concave. Orientation: Initially upright, then perpendicular to vertical. Number of ray florets per inflorescence: About 142 in numerous whorls. Color: When opening, upper and lower surfaces: Close to 187A to 187B. Fully opened, upper surface: Close to 9A overlain with 53A. Fully opened, lower surface: Close to 9C underlain with 59A.

*Disc florets.*—Shape: Tubular; apex dentate, five-pointed. Length: About 4 mm. Width, apex: About 1.5 mm. Width, base: About 1 mm. Number of disc florets per inflorescence: About 15. Color: Immature: Close to 154A. Mature: Apex: Close to 9A. Mid-section: Close to 144B. Base: Close to 155D.

*Phyllaries.*—Quantity per inflorescence: About 18. Length: About 6 mm. Width: About 2 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: Close to 147A.

*Peduncle.*—Length: First peduncle: About 4 cm. Forth peduncle: About 4.5 cm. Seventh peduncle: About 4.9 cm. Diameter: About 1.25 mm. Strength: Strong. Aspect: About 30° from vertical. Texture: Pubescent. Color: 146A.

*Reproductive organs.*—Androecium: Present on disc florets only. Anther color: 9A. Pollen: None observed. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0 to more than 38° C.

It is claimed:

1. A new and distinct cultivar of *Chrysanthemum* plant named 'Yocarmella', as illustrated and described.

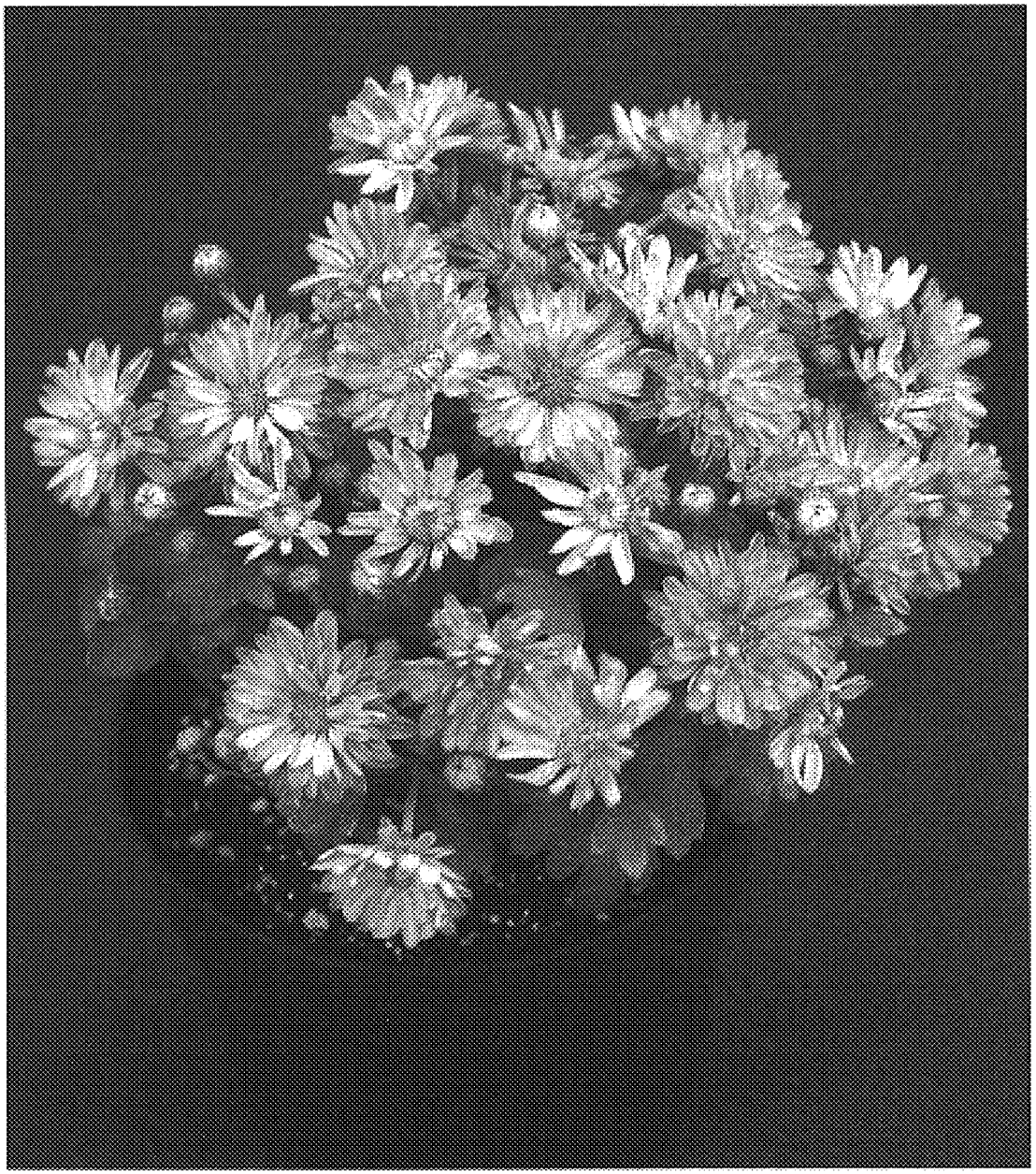

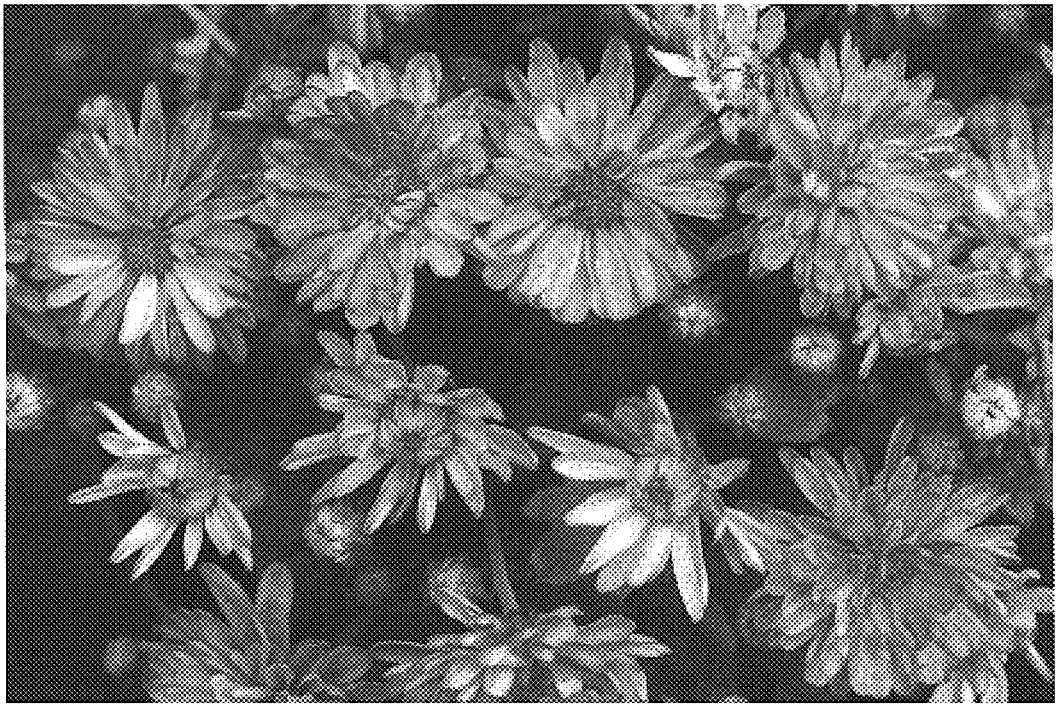

* * * * *